United States Patent [19]

Moessner

[11] Patent Number: 5,573,952
[45] Date of Patent: Nov. 12, 1996

[54] PROCESS FOR CONTROLLING CONCENTRATION OF A SOLUTION OF A SOLVENT AND POLYMER

[75] Inventor: Richard C. Moessner, Midlothian, Va.

[73] Assignee: E. I. Du Pont de Nemours and Company, Wilmington, Del.

[21] Appl. No.: 289,558

[22] Filed: Aug. 12, 1994

[51] Int. Cl.$^6$ .................................................. G01N 21/35
[52] U.S. Cl. .................................. 436/8; 436/50; 436/52; 436/55; 436/60; 436/139; 436/140; 436/164; 436/171; 422/62; 422/67; 422/82.05; 422/105; 250/339.12
[58] Field of Search ................................. 436/8, 50, 52, 436/55, 60, 139, 140, 164, 171, 179; 422/62, 67, 82.05, 105, 108; 208/DIG. 1; 364/497, 498, 500; 250/301, 339.6, 339.12

[56] References Cited

U.S. PATENT DOCUMENTS

| | | | |
|---|---|---|---|
| 4,272,481 | 6/1981 | Ahlstrom, Jr. et al. | 422/62 |
| 4,621,062 | 11/1986 | Stewart et al. | 436/55 |
| 4,836,999 | 6/1989 | Reed et al. | 423/574 R |
| 5,015,856 | 3/1990 | Gold | 250/339 |
| 5,145,785 | 12/1990 | Maggard et al. | 436/8 |
| 5,206,176 | 4/1993 | Beér et al. | 436/140 |
| 5,223,714 | 6/1993 | Maggard | 250/343 |
| 5,348,645 | 9/1994 | Maggard et al. | 208/209 |
| 5,403,552 | 4/1995 | Pardikes | 422/62 |

OTHER PUBLICATIONS

W. G. Fateley et al, The Tenets for Using Electromagnetic Radiation in Analytical and Structural Chemistry, *CPAC Informational Document Announcement #53*, 1–28, Aug. 9, 1994.

Roger E. Schirmer, Remote Optical Monitoring of Polymer Processing Over Long Fiber Optic Cables, *Guided Wave*, 28, No. 2, 65–69.

*Primary Examiner*—Jeffrey R. Snay
*Assistant Examiner*—Long V. Le

[57] ABSTRACT

A process for measuring and controlling the concentration of a solution at an aim point of an amide solvent and aramid polymers having aromatic and aliphatic carbon-hydrogen bonds that overlap using a near-infrared analyzer.

4 Claims, 3 Drawing Sheets

PROCESS FOR CONTROLLING CONCENTRATION OF A SOLUTION OF A SOLVENT AND POLYMER

BACKGROUND OF THE INVENTION

This invention relates to the determination of percent polymer solids dissolved in solvent and controlling the polymer solids concentration of the solution at an aim point using near-infrared spectroscopy.

It is known from the prior art that there is a correlation between the absorbance in the near-infrared of some physical or chemical property of a system. The techniques for using this correlation to control a process are usually very complex and none are known for determining and controlling the concentration of a polymer solution.

SUMMARY OF THE INVENTION

A process for measuring and controlling the concentration of a solution at an aim point of an amide solvent and aromatic polyamide polymers having aromatic and aliphatic carbon-hydrogen bonds that overlap using a near-infrared analyzer, said process comprising the steps of:

a) obtaining averaged absorbance spectra of the solution;

b) making a baseline correction to the spectra;

c) determining area-based contributions to the spectra from aromatic carbon-hydrogen bonds;

d) determining area-based contribution to the spectra from aliphatic carbon-hydrogen bonds;

e) computing the polymer concentration by utilizing a ratio-based algorithm with the area-based contributions of the aromatic and aliphatic carbon-hydrogen bonds as inputs;

f) scaling the polymer concentration from step e) in terms of percent aromatic polymer solids dissolved in the solvent;

g) adjusting the amount of solvent in the solution in accordance with percent aromatic polymer solids dissolved in the solution as determined in step f).

DETAILED DESCRIPTION OF THE INVENTION

This invention provides improved process control of the concentration of aromatic polyamide polymer solutions, particularly solutions of aramid polymers in amide solvents. Aromatic polymers useful in this invention include poly(metaphenylene isophthalamide), and other aramid polymers. By "aramid" is meant a polyamide wherein at least 85% of the amide (—CONH—) linkages are attached directly to two aromatic rings. Additives can be used with the aramid and, in fact, it has been found that up to as much as 10 percent, by weight, of other polymeric material can be blended with the aramid or that copolymere can be used having as much as 10 percent or other diamine substituted for the diamine of the aramid or as much as 10 percent of other diacid chloride of the aramid. Aromatic polyamide polymers useful in this invention are disclosed in U.S. Pat No. 3,287,324 to Sweeny and U.S. Pat No. 3,063,966 to Kwolek, both of which are incorporated by reference. Solvents useful in this invention include amide solvents like dimethyl acetamide, dimethyl formamide, n-methyl pyrrolidone, and the like. Aramid polymers are made by polymerizing an aromatic diamine and an aromatic diacid in an amide solvent. After the polymerization, excess solvent is removed to achieve adequate solution viscosities to form fibers, films, and the like.

Figure 1:
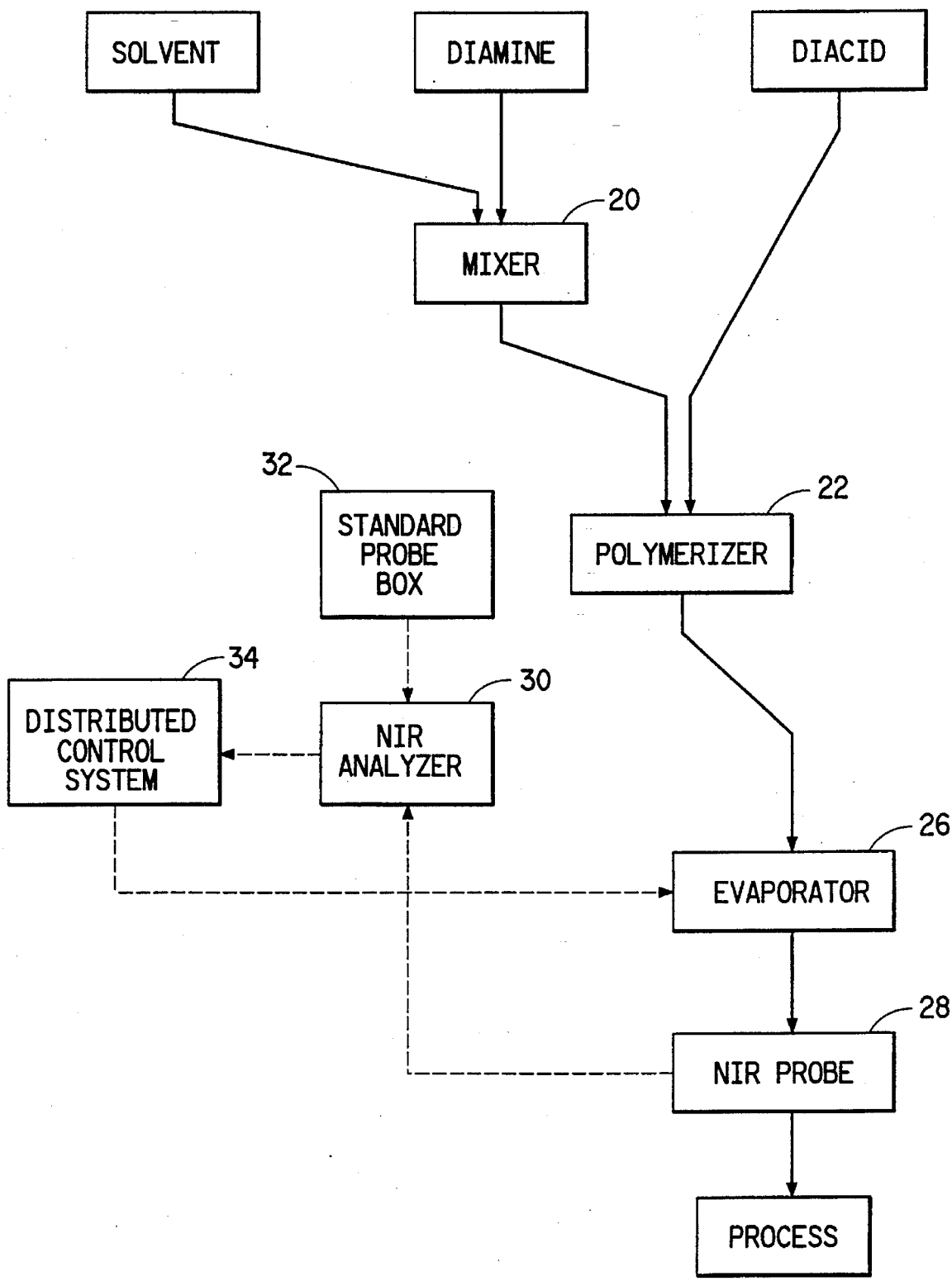
FIG. 1 is a flowsheet of a solutioning process for an aromatic polymer using a near-infrared analyzer for measuring and controlling the process.

As shown in FIG. 1, a solution of a diamine, typically metaphenylene diamine, and solvent, typically dimethyl acetamide, is made by adding diamine to the solvent and mixing in a mixer 20. The solution is then mixed with a diacid, typically isophthalic acid, in a polymerizer 22 to form a polymer solution. The polymer solution is then collected in an evaporator 26. The absorbance of the polymer solution in the evaporator is continuously determined by a near-infrared radiation (NIR) probe 28, which outputs a process signal to a NIR analyzer 30. The NIR analyzer verifies the signal processing equipment is operating correctly by comparing the signal received by the process probe to a standard probe box 32 containing another probe and a multilayer standard. Once the accuracy of the process signal is verified, the analyzer computer processes the process signal and generates an output signal, representative of the concentration of the polymer solution in the evaporator, to a distributed control system 34. The distributive control system compares the output signal to the setpoint concentration and controls temperature and/or pressure in the evaporator to remove the excess solvent. The polymer solution can now be used in additional process steps to make fibers, films, and the like.

Figure 2:
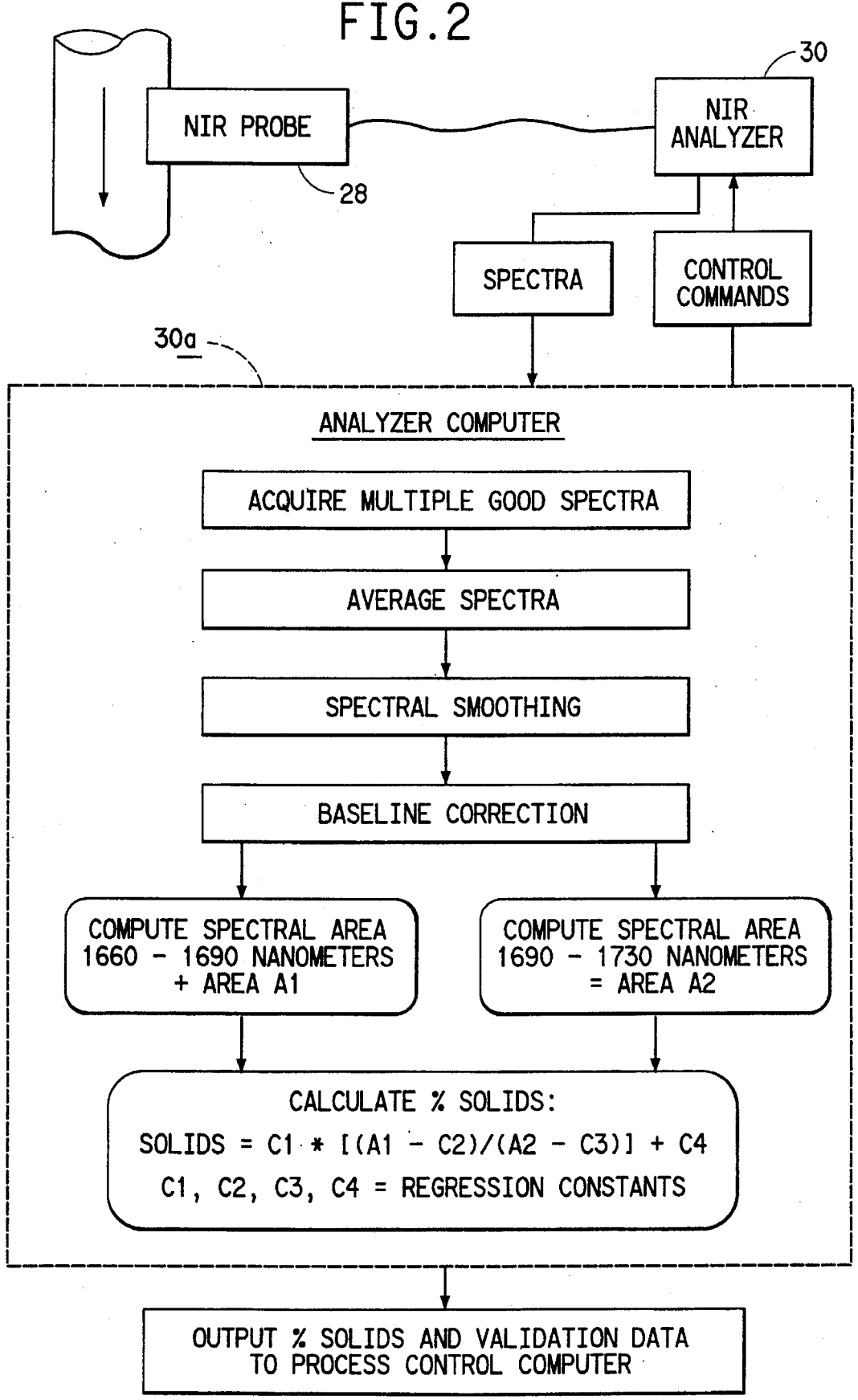
FIG. 2 represents a flowsheet of the computing steps performed in the near-infrared analyzer.

Referring now to FIG. 2, the NIR analyzer obtains a process signal from a NIR probe located on-line, and sends spectra to the analyzer computer 30a. The computer performs two functions, (1) sending control commands to the NIR analyzer, and (2) calculations on the spectra to determine percent concentration (or % solids). The calculations utilize multiple good spectra, on which they first average the measured values for the various wavelengths to generate an average spectra, smooth the spectra one or more times using 17-point spectral smoothing, and then apply a 2-point baseline correction. The computer then computes a first area formed beneath the spectra and bordered by 1660 to 1690 nanometers, the wavelengths representative of the aromatic carbon-hydrogen bond; and a second area formed beneath the spectra and bordered by 1690 to 1730 nanometers, the wavelengths representative of the aliphatic carbon-hydrogen bond. The areas for the aromatic and aliphatic carbon-hydrogen bonds are further illustrated by the shaded areas on FIG. 3. The computer uses these two areas and regression constants to make the final calculation for these two areas and regression constants to make the final calculations for percent solids, and this is outputted to the distributed control system.

Near-infrared (NIR) spectroscopy is conducted with specialized computerized equipment known as the near-infrared (NIR) spectrometer. There are several suppliers of such equipment, including UOP Guided Wave, El Dorado Hills, Calif.; NIR Systems, Silver Spring, Md.; and L. T. Industries, Inc., Rockville, Md. The equipment vendors normally supply, with their equipment, a comprehensive set of operating software, which permits the user to operate his or her NIR spectrometer and to analyze the data. A computer is attached to the spectrophotometer for control of the device and interpretation of the spectral data.

When one of these spectrophotometers is used to scan a sample or process sample stream, a lengthy series of discrete results are collected at each wavelength step by the instrument. The resulting response at each wavelength can be expressed in transmittance (T), reflectance, or absorbance (A) units, A being equal to log (1/T). When T=1, no absorption occurs; while when T=0, infinite absorption occurs. If these results are plotted vs. wavelength, a spectrum (curve) is produced.

There are many well-known mathematical techniques of correlation of NIR spectral responses. They include, for example, "Single-Term Linear Regression," "Multiterm Linear Regression," "Component Spectrum Reconstruction," and "Discriminant Analysis" methods explained in an article by W. R. Hruschka at pp. 35–55 of Near-Infrared Technology in the Agricultural and Food Industries, P. C. Williams et al., Editors, American Association of Cereal Chemists, Inc., St. Paul, Minn., 1987 ("Williams"). Other techniques include, for example, "Hruschka Regression, "Fourier Transform Regression," "Principal Component Regression," and "Partial Least Squares Regression" methods explained in detail in an article by H. Martens et al. at pp. 57–87 of Williams. In Chapter 3 of Multivariate Calibration, H. Martens et al., John Wiley & Sons, Ltd., Chichester, U.K. 1989, more techniques, including, for example, "Univariate Calibration," "Bilinear Modeling," "Self Deconvolution," "Target Transformation Factor Analysis," "Rank Annihilation Method," "Step-wise Multiple Linear Regression" "Ridge Regression," "Nonlinear Regression," and "Nonparametric Regression" are taught. The "Neural Network" technique explained in D. E. Rumelhart et al. in Parallel Distributed Processing-Explorations in the Microconstruction of Cognition, Vol. 1, Foundations 1986; and Vol. 2, Psychological and Biological Models, 1986; and Vol. 3, A Handbook of Models. Programs and Exercises, 1988, MIT Press Cambridge, Mass., may also be applied.

Some commercially available software packages include, for example, "Near-Infrared Spectral Analysis Software" (NSAS) by NIR Systems, Inc., Silver Spring, Md.; "Unscrambler" by Camo A/S, Trondheim, Norway; "Spectra Metrix," "LightCal," and "LightCal Plus" by L. T. Industries Corporation, Rockville, Md.; and "InfraAnalyzer Data Analysis System" (IDAS) and "Principal Component Analysis Program" (PCA-pc) by Bran+Luebbe Analyzing Technologies, Inc.

The composition of aramid polymerization process streams can be predicted by the application of near-infrared spectroscopy, within the wavelength range of 600–2500 nm, especially 1100–2500 nm. The method requires establishing a correlation between composition component of interest of samples of a training set and their near infrared spectra, developing from that correlation a predictive equation, verifying the accuracy of the predictive equation on samples of a validation set, and applying the predictive equation to the determination of the composition of unknown samples.

The absorbance may be measured as the absorbance, or as the first, second, third, fourth or higher derivative of absorbance or by other signal processing techniques. The signal can be used to control a multi-component process by manipulation of process control actuators which have known impacts upon the components to be controlled.

Multiple scans are made (2 or more) using in-line fiber-optic near-infrared probes operating in transmission. The transmittance or absorbance at each wavelength within the range of about 1000 to 2000 nanometers is stored for each nanometer wavelength separation in order to create each spectrum. The training set analyses are designed to encompass process conditions (temperature, pressure, concentrations, etc.) which are anticipated to be experienced by the process during routine in-line analyses. The spectra are then averaged. The averaged spectrum is then subjected to one or more spectral smoothing operations to further reduce noise in the spectral data. Spectral baseline correction is performed in most cases prior to storage or regression analysis. The spectrum is then stored together with analytical data in order to prepare a training set of known data for regression analysis. The training set is then subjected to various regression analysis methodologies in order to discover the most robust mathematical expression in the form of a predictive equation for calculating the desired measurement from the spectral responses. This process is repeated for each of the desired analytical measurement tasks.

The predictive mathematical expressions generated during the training process described above are then routinely applied to the in-line measurement of the same species in the process stream. The routine analyses are undertaken at process conditions which are within the envelope of conditions used during the training process. The routine spectra are subjected to the identical data treatments utilized with the training set spectra.

Near-infrared spectrometers and modified IR spectrometers of conventional design may be used with the invention. Preferred modes of operation are transmission, reflectance, and transflectance. Suitable spectrometers are the NIR Systems model 6500; LT Industries model 1200; and the Guided Wave model 300 series. The spectrometer can be operated on a batch basis (receiving signals, e.g. by a sample feeding arrangement), or, more preferably, on a continuous basis in which the fluid to be measured flows through a cell, or a probe immersed in the flowing fluid transmits optically through a fiber-optic cable to the spectrophotometer. The technique for sampling, measuring, and signal processing can be conventional and is well-known to those skilled in the art.

Figure 3:
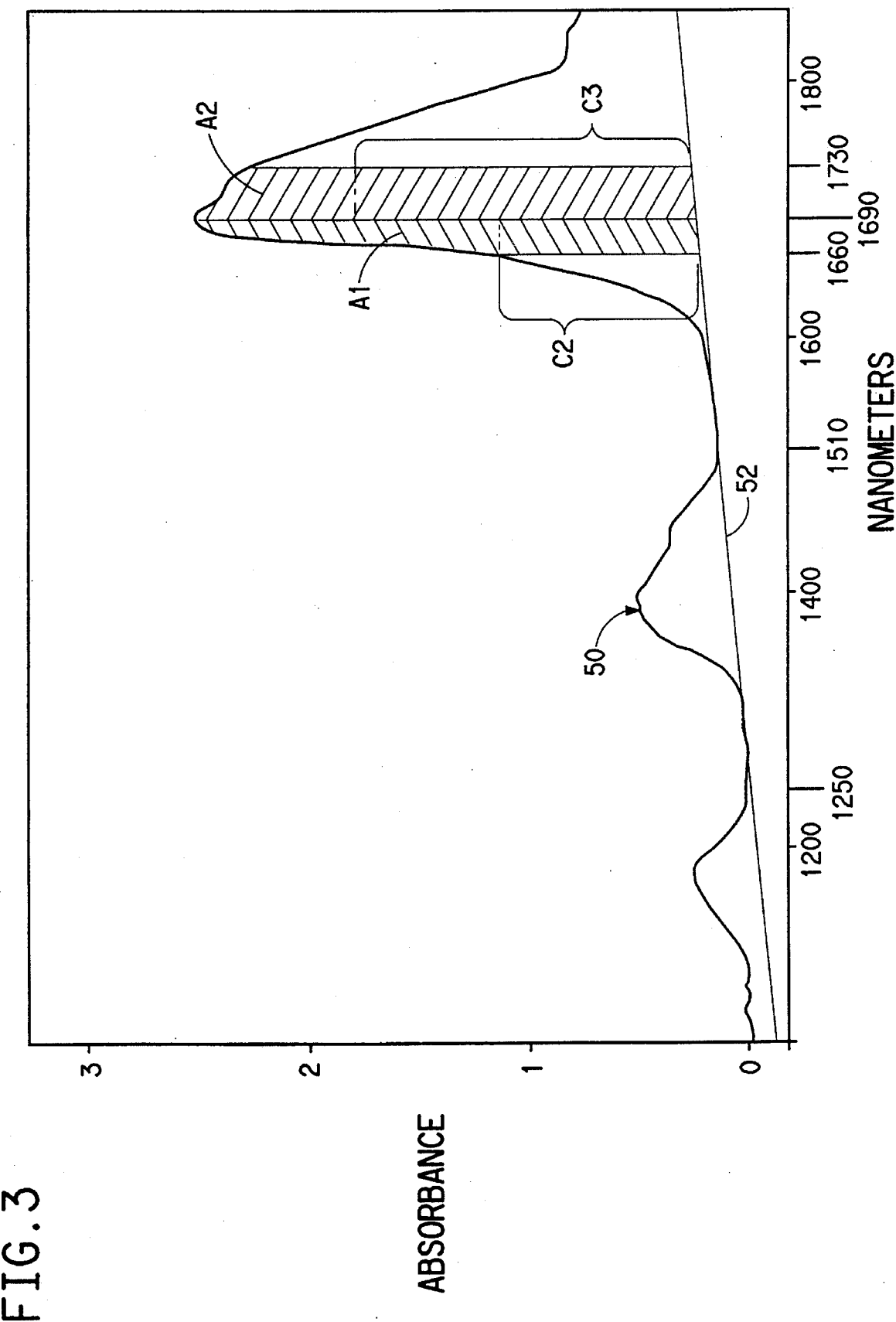
FIG. 3 illustrates the procedure for calculating the area based contributions of aromatic and aliphatic carbon-hydrogen bonds in an absorbance spectrum in a solutioning process such as described in conjunction with FIG. 1.

A new method has been developed in the form of area-based evaluations of spectral data as opposed to conventional evaluations based upon the absorbance values at specific wavelengths. In the new method, area averages are derived by mathematical determination of the area beneath an absorbance vs. wavelength spectrum between two specific wavelengths. Such area averages may then be further treated by baseline correction, constant area subtraction, or combination with other appropriate area averages. Referring now to FIG. 3, a spectrum 50 is produced having wavelengths in nanometers along the x-axis and magnitude of absorbance along the y-axis. The three measurements of the magnitude of the absorbance for each wavelength are averaged so you have one spectrum 50 composed of the averaged magnitude of the absorbance for each wavelength.

The spectrum is smoothed twice utilizing a Savitsky-Golay smoothing algorithm employing 17 spectral data points (center wavelength and 8 nm on either side).

This is done to improve the signal-to-noise ratio. This is just one technique known by persons skilled in the art.

The studies of Savitsky and Golay are among the early developments of least-squares polynomial smoothing in analytical chemistry. They have demonstrated that the noise in every window is reduced by a factor approximately equal to the square root of the span of the window, provided the noise is normally distributed. Note, however, that the larger the window the higher the loss of resolution. They have also tabulated the coefficients needed for the smoothing formulas using various models (e.g., quadratic and higher-order polynomials and their derivatives) and various window spans. (A. Savitsky and M. J. E. Golay, "Smoothing and Differentiation of data by Simplified Least Squares Procedures," Anal Chem. 36, 1627 1964).

The baseline is corrected by drawing a line 52 between the two spectral valleys located at 1250 and 1510 nanometers. This line extends beneath the region we are evaluating for solids (1660–1730 nanometers, nm).

The area A1 between the baseline and the spectrum between 1660–1730 nm is measured. This represents the aromatic carbon-hydrogen bonds in solution.

The area A2 between the baseline 52 and the spectrum between 1600–1730 nm is measured. This represents the aliphatic carbon-hydrogen bonds in solution.

These areas A1 and A2 are different in size and also represent a lot of "dead area" (unchanging) below the regions which may change as % solids change.

The constant areas C2 and C3 of each of the areas A1 and A2, respectively, are subtracted in order to make the areas (A1–C2) and (A2–C3) of similar size and to reduce the unchanging area domains. By doing this, a set of areas are derived which are more sensitive to small changes in % solids. In FIG. 3, arbitrary areas are selected from both shaded areas A1 and A2, and these areas are designated C2 and C3. The only stipulation is that the quantity A1–C2 be approximately equal to the quantity A2–C3 for the desired setpoint concentration.

The ratio (A1–C2)/(A2–C3) varies with % solids, but needs to be scaled in engineering units (% aramid polymer solids in DMAC solution).

It is scaled using two constants which provide slope (C1) and intercept (C4) correction. C1 and C4 are useful in on-going support of the measurement since small changes to C4 allow minor adjustments to rezero the measurement, while small changes to C1 allow adjustments to the span or sensitivity of the measurement.

$$C1 * \frac{(A1 - C2)}{(A2 - C3)} + C4 = \text{Concentration}$$

which is essentially an equation of the form:

$$ax+b=y$$

where a is the slope, b is the intercept, x is the ratio of the areas under the curve, and y is the concentration. Obviously, a is C1 and b is C4.

The constants C1 and C4 need to be specified for use in controlling the process. They can be found by using solutions of known concentration and multiple linear regression. They can be determined by generating two spectra of two solutions having different but known concentrations which gives a "y" for each solution, and then calculating the ratio of the areas under the curve, which gives an "x" for each solution, which in turn gives you two equations and two unknowns which can be solved for C1 and C4.

So, in practice, C1 and C4 are known and you calculate from the spectra the value of "x." "y" can be determined and then fed to any process control apparatus.

Based on the information obtained by the spectral analysis, the amount of solvent in the solution can then be automatically adjusted in any appropriate means, including evaporation.

What is claimed is:

1. A process for measuring and controlling the concentration of a solution at an aim point of an amide solvent and aramid polymers having aromatic and aliphatic carbon-hydrogen bonds that overlap using a near-infrared analyzer, said process comprising the steps of:

a) obtaining averaged absorbance spectra of the solution for the wavelengths where the contributions to the spectrum by aromatic and aliphatic carbon-hydrogen bonds overlap;

b) making a baseline correction to the spectra;

c) determining area-based contributions, A1, to the spectra from aromatic carbon-hydrogen bonds;

d) determining area-based contributions, A2, to the spectra from aliphatic carbon-hydrogen bonds;

e) computing a ratio (A1–C2)/(A2–C3) by utilizing a ratio-based algorithm with the area-based contributions of the aromatic and aliphatic carbon-hydrogen bonds as inputs wherein C2 and C3 are constants;

f) scaling the ratio, (A1–C2)/(A2–C3) from step e) using known polymer concentrations and multiple linear regression to provide a corrected slope and intercept so that the percent of aromatic polymer solids dissolved in the solvent is determined; and g) adjusting the amount of solvent by removing excess solvent from the solution in accordance with percent aromatic polymer solids dissolved in the solution as determined in step f).

2. The process of claim 1 wherein the aromatic polyamide polymer is an aramid polymer.

3. The process of claim 1 wherein the aromatic polyamide polymer is poly(meta-phenylene isophthalamide).

4. The process of claim 1 wherein the amide solvent is dimetyl acetamide.

* * * * *